(12) United States Patent
White et al.

(10) Patent No.: US 9,360,296 B2
(45) Date of Patent: Jun. 7, 2016

(54) SYSTEM FOR CALCULATION OF MATERIAL PROPERTIES USING REFLECTION TERAHERTZ RADIATION AND AN EXTERNAL REFERENCE STRUCTURE

(71) Applicant: Picometrix, LLC, Ann Arbor, MI (US)

(72) Inventors: Jeffrey S. White, Manchester, MI (US); David Zimdars, Ann Arbor, MI (US)

(73) Assignee: PICOMETRIX, LLC, Ann Arbor, MI (US)

( * ) Notice: Subject to any disclaimer, the term of this patent is extended or adjusted under 35 U.S.C. 154(b) by 0 days.

(21) Appl. No.: 14/436,073

(22) PCT Filed: Oct. 18, 2013

(86) PCT No.: PCT/US2013/065671
§ 371 (c)(1),
(2) Date: Apr. 15, 2015

(87) PCT Pub. No.: WO2014/063044
PCT Pub. Date: Apr. 24, 2014

(65) Prior Publication Data
US 2015/0268030 A1    Sep. 24, 2015

Related U.S. Application Data

(60) Provisional application No. 61/716,255, filed on Oct. 19, 2012.

(51) Int. Cl.
*G01B 9/02* (2006.01)
*G01N 21/35* (2014.01)
*H04J 14/02* (2006.01)

(52) U.S. Cl.
CPC .............. *G01B 9/02001* (2013.01); *H04J 14/02* (2013.01)

(58) Field of Classification Search
CPC ......................... G01B 9/02001; G01N 21/3581
USPC ........................................... 250/341.1, 341.8
See application file for complete search history.

(56) References Cited

U.S. PATENT DOCUMENTS

| 4,678,915 A | 7/1987 | Dahlquist et al. |
| 7,345,279 B2 | 3/2008 | Mueller |
| 7,693,571 B2 | 4/2010 | Arnone et al. |
| 7,808,636 B2 | 10/2010 | Schulkin et al. |

FOREIGN PATENT DOCUMENTS

WO    WO 2010/126872 A1    11/2010

*Primary Examiner* — Mark R Gaworecki
(74) *Attorney, Agent, or Firm* — Brinks Gilson & Lione (57) ABSTRACT

A system for interpreting terahertz radiation includes a terahertz transmitter configured to output a pulse of terahertz radiation and a terahertz receiver configured to receive at least a portion of the pulse of radiation from the terahertz transmitter. The terahertz receiver is configured to output a signal based on the radiation received by the terahertz receiver.

20 Claims, 7 Drawing Sheets

SYSTEM FOR CALCULATION OF MATERIAL PROPERTIES USING REFLECTION TERAHERTZ RADIATION AND AN EXTERNAL REFERENCE STRUCTURE

CROSS REFERENCE TO RELATED APPLICATIONS

This application is a nationalization of PCT Serial No. PCT/US2013/065671, filed Oct. 18, 2013 which claims benefit of U.S. Provisional Application Ser. No. 61/716,255, filed Oct. 19, 2012.

BACKGROUND

1. Field of the Invention

The present invention generally relates to systems and methods for calculations of material properties using terahertz radiation.

2. Description of Related Art

Reflection time domain terahertz ("TD-THz") transmitters can project a pulsed terahertz ("THz") beam into a dielectric material under measurement, sometimes called a sample. Such materials may be paper, coated paper, plastic sheet, non-woven materials (fiber, cloth), extruded insulation, foams, adhesives and similar materials.

However, measuring material properties of these dielectric materials under measurement can be complicated by the fact that the reflection of the THZ radiation will impacted based on the position of the sample. If the position of the sample cannot be determined, the measurement of the material properties will be adversely impacted.

SUMMARY

A system for interpreting terahertz radiation includes a terahertz transmitter configured to output a pulse of terahertz radiation and a terahertz receiver configured to receive at least a portion of the pulse of radiation from the terahertz transmitter. The terahertz receiver is configured to output a signal based on the radiation received by the terahertz receiver.

The system also includes a first optical interface providing optical interference to the pulse of terahertz radiation from the terahertz receiver. The first optical interface will reflect a first optical interface reflected portion of the pulse of terahertz radiation to the terahertz receiver. The system also includes a second optical interface providing optical interference to the pulse of terahertz radiation. A second optical interface will reflect a second optical interface reflected portion of the pulse of terahertz radiation to the terahertz receiver. A spacing is defined between the first and second optical interfaces. The spacing is configured to receive the sample to be radiated by at least a portion of the pulse of terahertz radiation. The sample will reflect a first sample reflected portion of the pulse of terahertz radiation to the terahertz receiver and a second sample reflected portion of the pulse of terahertz radiation to the terahertz receiver.

Generally, the terahertz transmitter and the terahertz receiver are disposed substantially adjacent to one another in a housing. A processor may be in communication with the terahertz receiver and configured to receive the signal from the terahertz receiver. The process is then configured to determine caliber thickness, density, index over fraction or mass of the sample based on the signal. The system may also include a gantry, wherein the housing is coupled to the gantry as configured to move the housing across a sample.

The first optical interface may be mounted to the housing, or may be located between the terahertz transmitter and the sample. The second optical interface may be mounted to the gantry or may simply be mounted opposite of the first optical interface.

The system may also include a position sensor in communication with the processor. The position sensor is configured to determine the distance of the space in between the first optical interface and the second interface and output a distance signal to the processor. The position sensor may be a temperature sensor or may be an eddy current sensor.

Further objects, features and advantages of this invention will become readily apparent to persons skilled in the art after a review of the following description, with reference to the drawings and claims that are appended to and form a part of this specification.

DETAILED DESCRIPTION

Figure 1:
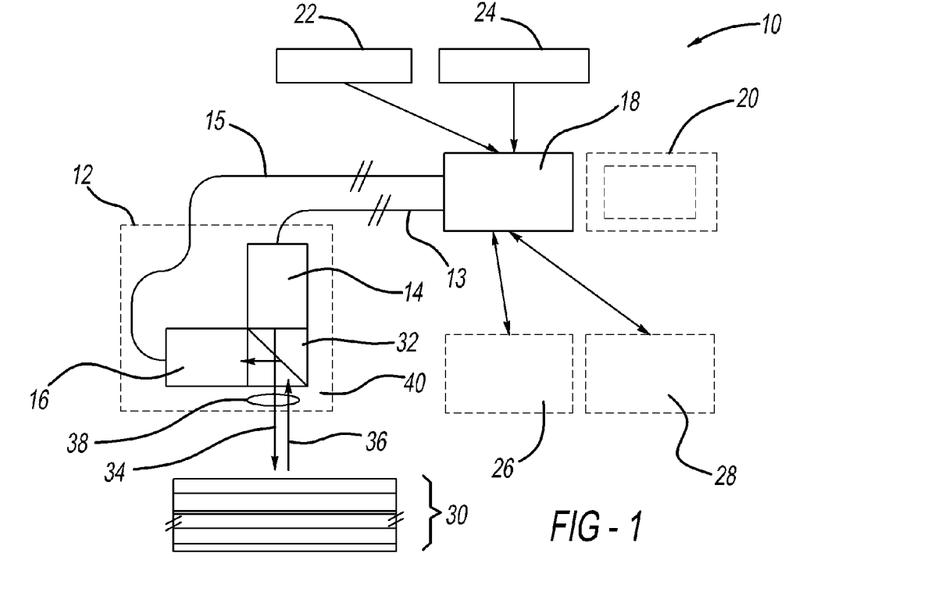
FIG. 1 illustrates a block diagram of a traditional time domain based terahertz system.

Referring to FIG. 1, a system 10 for interpreting terahertz radiation is shown. As its primary components, the system includes a housing 12 having a terahertz transmitter 14 and terahertz receiver 16 contained within. The system 10 also includes a terahertz control unit 18, such as an optical laser source and a computer system 20. The optical laser source 18 may be coupled to the terahertz receiver 16 and/or terahertz transmitter 14 via umbilicals 13 and 15. The umbilicals 13 and 15 may be 0-100 meters long. Flexible fiber optic/electrical umbilicals 13 and 15 can be put in flexible cable tray ("snake") when the TD-THz sensor is mounted on a motion control gantry scanning over the web. The umbilicals 13 and 15 optically couple the laser source 18 to the terahertz receiver 16 and/or terahertz transmitter 14.

The computer system 20 may be coupled either directly or indirectly to the terahertz receiver 16, so as to receive a signal from the terahertz receiver 16. The computer system 20 can then interpret the signal from the terahertz receiver 16 so as to interpret the radiation received by the terahertz receiver 16. The system 10 may also include a variety of separate sensors 22 and 24. These sensors 22 and 24 may include positioning sensors and/or temperature sensors.

The system 10 may also include a feedback control unit 26 to control the production of material and may also include a motion control 28 for controlling a gantry which will move the housing 12 across the sample or material under test 30 so that measurements may be made. The sample 30 may be any type of a sample but generally is a sample having multiple layers such as paper or other type of webbing material.

The housing 12 may further include a beam splitting device 32, such as a beam splitting cube. The beam splitting device 32 directs terahertz radiation 34 from the terahertz transmitter 14 towards the sample 30. In like manner, the beam splitting device 32 directs radiation 36 from the sample that was originally transmitted from the terahertz transmitter 14 to the terahertz receiver 16. In addition, a lens 38 may be used to focus the terahertz radiation sent to or from the sample 30 generally through a first port 40.

Figure 2:
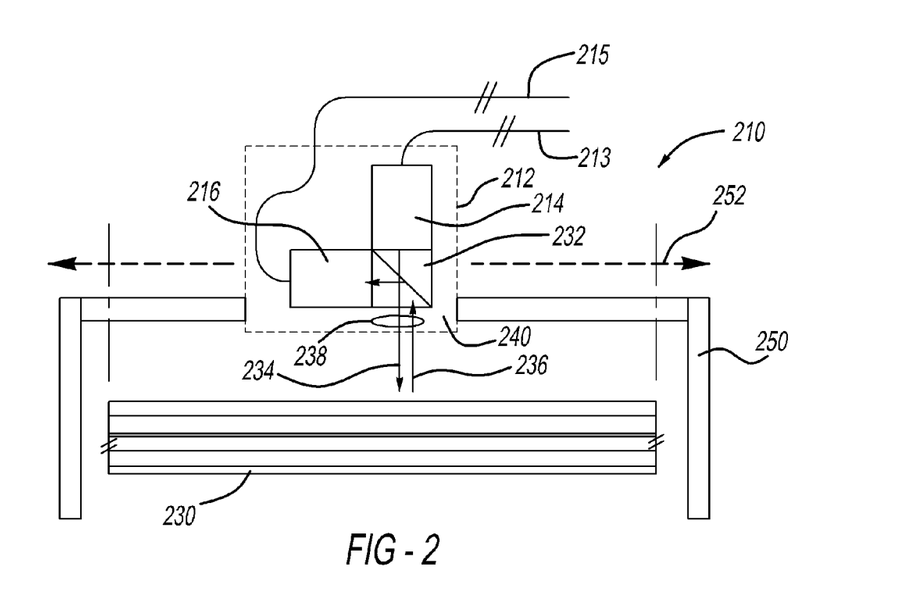
FIG. 2 illustrates the system of FIG. 1 mounted on a gantry over a web of sheet material.

Referring to FIG. 2, a more detailed description of the system 210 is shown. In this embodiment, like reference numerals are used to refer to like elements with the exception that the number "2" has been placed in front of these elements. A description of these elements will not be given again. In this embodiment, a gantry 250 is located above a sample 230. Here, the housing 212 is mounted to the gantry 250 such that the housing moves along the length of the sample 30 as indicated by arrow 252.

The terahertz receiver 216 and/or terahertz transmitter 214 may be in a monostatic, or collinear configuration. In this configuration, the THz beam of pulses projected to the material under test 30 and the reflections from the interfaces within the material under test 30 (and from external reference structure interface(s), if present) follow the same path. This configuration is usually preferred as it eliminates parallax effects and maximizes the reflection power from the sample. This collinear configuration is particularly important when the material under test is moving up and down with respect to the THz sensor. As an alternative, a pitch-catch arrangement could be used, particularly for very thin materials which are not moving up and down.

The terahertz receiver 216 and/or terahertz transmitter 214 are shown has having an objective to focus and collect the THz beam probing the material under test 230. The objective may be a lens 238, curved mirrors, or a combination. The objective may have a fixed focal length, may be interchangeable, or may be a variable focal length lens. A single element may be used or multiple elements may be used. Some configurations may not require an objective.

The dashed line around the terahertz receiver 216 and/or terahertz transmitter 214 is a nominal housing 212 which protects the sensor from the elements (humidity, dust) and mechanical impact. The sensor may or may not be enclosed in such a housing.

The terahertz receiver 216 and/or terahertz transmitter 214 is shown with the transmitter and receiver antenna mounted in a remote, freely positionable head connected with flexible fiber optic/electrical umbilicals to the control unit. This is a preferred embodiment because the sensor head may be made as small and rugged as possible, by placing the laser, power supply, optical delay scanner, computer and/or other electronics in the TD-THz control unit. The control unit may be mounted safely away from the scanning area. It could be placed in an environmentally controlled cabinet.

Alternate terahertz receiver 216 and/or terahertz transmitter 214 may be employed. As practicable, some or all of the systems in the TD-THz control unit may be miniaturized and placed entirely in the TD-THz sensor head. Such an all-in-one configuration may not necessarily employ fiber optics. The terahertz transmitter and receiver may be on separate mounts or mechanically co-located. The terahertz receiver 216 and/or terahertz transmitter 214 may share the same laser, electronic, and/or other support sub-systems co-located with transmitter and/or receiver (in an all-in-one fashion); or laser, electronic, and/or other support subsystems may be remotely located from the transmitter and/or receiver, connected by an electrical and/or fiber optic cable.

The terahertz receiver 216 and/or terahertz transmitter 214 may operate on the principle of cross-correlating noise pulses triggered by a broad-band source instead of using single pulses generated from a femtosecond laser. Any method of generating THz EM may be employed.

The terahertz receiver 216 may operate in the frequency-domain instead of the time-domain. If the terahertz receiver 216 operates in the frequency domain, the transmitter may as well. The terahertz transmitter 214 and receiver 216 must have sufficiently broad bandwidth to achieve the desired resolution for the measurement of a layer thickness of the sample. The terahertz transmitter 214 may be pulsed or not, as long as it has sufficient bandwidth. The terahertz transmitter 214 emits a broad-band terahertz beam which reflects both from one or more layer interfaces of the sample as well as any external reference structure interfaces. The frequency-domain terahertz receiver 214 records the reflection as a function of frequency amplitude and/or phase. The recorded frequency-domain data can then be transformed into the time-domain through the use of a mathematical transform (such as the Fourier transform). This data transformed into the time-domain will now represent the time-of-flight of interfaces within the sample and the external reference interfaces in the same or similar manner as data collected natively in the time-domain; and the material properties of the sample 230 can be calculated using the compensation methods in the same manner as the native time-domain data. Alternatively, the computation of the material properties could be made from the frequency-domain amplitude and/or phases directly. Two or more peaks in the time-domain corresponding to reflection interfaces separated with particular time-of-flight interval(s) are represented by loss and/or transmission peaks spaced with particular frequency spacing(s) in the frequency-domain. These frequency-domain spacings could be used to calculate the same material properties using the known external reference interface spacings from one or more of the compensation schemes described. Alternate frequency domain methods include the frequency modulated continuous wave method (FMCW).

Figure 3:
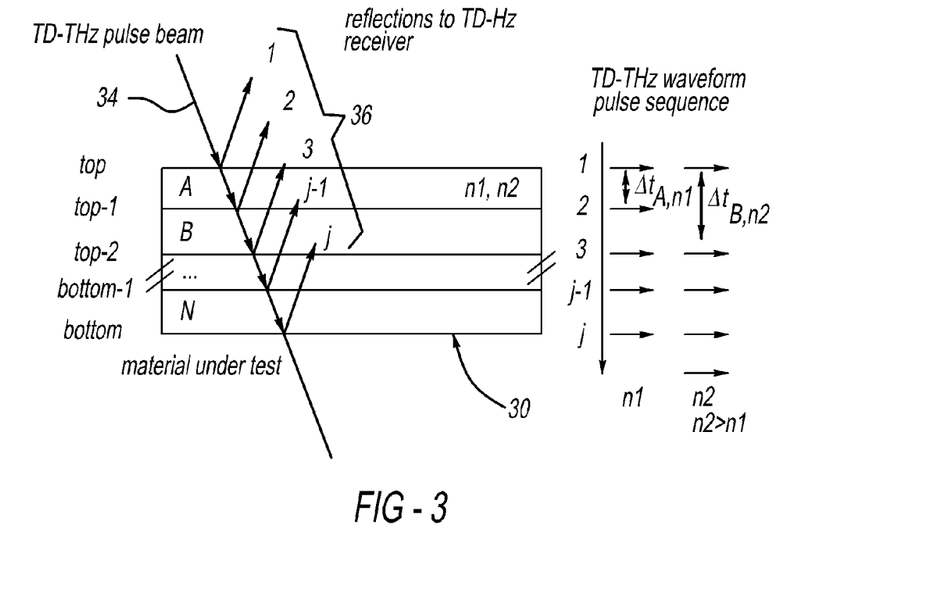
FIG. 3 illustrates a cross section of material under testing without a second optical interface, sometimes referred to as an external reference structure.
Figure 4:
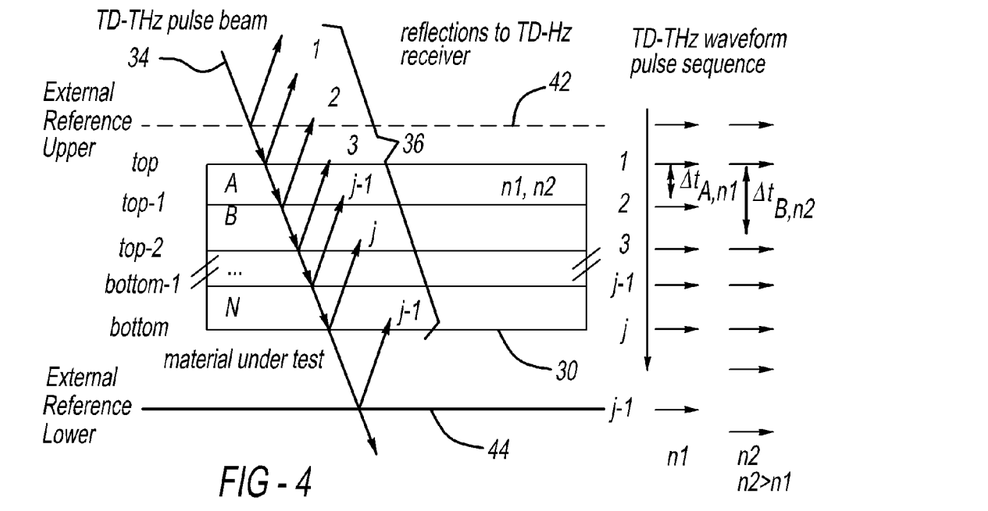
FIG. 4 is a cross section of material under test with a second optical interface.

Referring to FIGS. 3 and 4, these figures illustrate what occurs to the beam of terahertz radiation as it comes in contact with the sample 30. The beam of terahertz radiation 34 is reflected by each surface of each layer of the sample 30. These reflected portions of the terahertz radiation are then sent back to the terahertz receiver 16 of FIG. 1. FIG. 4 illustrates a system having a first optical interface 42 and a second optical interface 44. The first optical interface 42 may be partially transmissive while the second optical interface 44 may be completely reflective, such as a mirror. In this situation, radiation 34 is reflected by each layer of the sample 30 but also by the first optical interface 42 and the second optical interface 44. These reflected portions of the terahertz beam 34 form the reflected terahertz radiation 36 that is sent back to the terahertz receiver 16 of FIG. 1.

The sample 30 will have at least 2 reflection interfaces (top and bottom outer surfaces) and may or may not have one or more internal interfaces. The optical interfaces 42 and 44 may be used to create one or more additional external interfaces placed above and/or below the material under measurement. The relative timing of one or more of the reflection pulses from the sample 30, and one or more of the reflection pulses from the optical interfaces 42 and 44, can be used to calculate properties of the sample 30 such as caliper thickness, density, index of refraction and mass. These values are calculated using one or more calibration coefficients times a linear combination of the appropriate sum and/or differences of interface pulse times. As stated previously, the terahertz receiver 16 may be static or it may move. These optical interfaces 42 and 44 may be static and may or may not be connected to the housing 12 and/or the structure may move with the housing 12. The terahertz receiver 16, sample 30 and optical interfaces 42 and 44 are geometrically configured such that each of the sample interfaces and the optical interfaces 42 and 44 will result in a reflection pulse recorded in the TD-THz waveform. The relative timing of one or more of these material under measurement reflection pulses and one or more of the optical interfaces 42 and 44 can be used to calculate material properties of the material under measurement such as caliper thickness, density, index of refraction and mass.

These values are calculated using one or more calibration coefficients times a linear combination of the appropriate sum and/or differences of interface pulse times. The optical interfaces 42 and 44 are built to have a known or measureable (i.e., defined) distance between the optical interfaces 42 and 44. The separation between all external interfaces must be measureable on the timescale of the collection of one or more TD-THz waveforms.

The fixed distance(s) between the optical interfaces 42 and 44 are known or measured. These known interface separation distances are used, in combination with TD-THz reflection pulse time derived values, to calculate certain material properties which would be ambiguous from the TD-THz measurement alone (e.g., density) or without certain of the external interfaces. The defined distances between the external interfaces can also be used to accommodate for: 1) shifts in the absolute timing of the TD-THz pulse (e.g. due to fiber optic stretching) 2) changes in the index of refraction of the material under measurement; 3) changes in the density of the material under measurement; 4) and other effects.

These optical interfaces 42 and 44 must have either; 1) high geometric stability so a previously collected stored measurement can be used 2) the interface distances be measured with sufficient precision over short (the length of single TD-THz waveform measurement 0.001 to 1 s) and longer times (minutes, hours or days) or indirectly measurement or determined from ancillary sensors and calibrations methods (e.g., thermocouples and calibration method to temperature). The geometric stability required is often less than 2 microns. The structure must be built to reduce microphonic and other vibrations to within the required tolerance. In some cases the structure must span several meters over a wide sheet of material under measurement. In this case, the optical interfaces 42 and 44 structure may change its geometric distance(s) over minutes, hours or days due to thermal expansion or contraction, or due to some change external stress.

The cross-sectional diagram of the material under test 30 shown the timing of the TD-THz reflection pulses, without an external reference structure, is shown in FIG. 3. The material is shown having one or more layers (the number denoted by N) labeled A, B, . . . , N. There are j=N+1 interfaces. The top and bottom interfaces are usually with an air boundary, but they need not be. The reflections from the interfaces are labeled 1, 2, . . . , j−1, j. The sequence and timing of reflection pulses is shown on the right side of the Figure. FIG. 3 shows the reflections at an angle. This illustration method is for clarity purposes only. The reflections may be normal or at an angle.

Each of the "N" layers has a mechanical thickness "L" which may vary in each location and an effective index of refraction "η". If the index of refraction η is known, then the thickness of the layer can be derived from the TD-THz waveform by:

$$L = c \cdot t / (2 \cdot n),$$

where c is the speed of light in vacuum.
Alternately the effective index of refraction of the layer can derived if the thickness L is held to a known value.

The index of refraction is a function of the material chemical and physical composition, and may be proportional to the density of the material, for example. The effective index of refraction is not usually constant. It may vary with density, for example. The right side of FIG. 3 shows that if the index of one layer increases, then the timing between the peaks increases, even if the mechanical thickness remains constant. This creates an ambiguity in the calculation of the thickness of the material under test from the TD-THz data from the timing peaks alone. If it was incorrectly assumed that the index remained constant, an increase in density of a layer would look (incorrectly) like an increase in thickness of that layer.

One key measurement, that a varying index of refraction of one or more layers makes ambiguous, is the overall physical "caliper" thickness of the material. The overall sample caliper thickness can be calculated if an additional "external reference structure" or ERS or first optical interface 42 and second optical interface 44 is added around or near the sheet sample. An example cross-sectional diagram of the material under test shown the timing of the TD-THz reflection pulses, with an external reference structure, is shown in FIG. 4. The upper and lower surfaces of the ERS are a known or measured distance apart, D. The distance D is either known from the design or measured dimensions of the ERS prior to the measurement of the material under test. This disclosure discloses the method(s) of determining the ERS dimension D at points during or very close in time to the sample measurement process. U.S. patent application Ser. No. 12/667,986 is herein incorporated by reference in it's entirely.

Ideally, the upper surface of the ERS transmits the majority of the THz beam. The bottom surface of the ERS must be at least partially reflective, and may be a mirror. The time of flight of the THz pulses 0 and j+1 corresponding to the upper and lower surfaces in air is:

$$T_{ERS} = 2 \cdot D / C$$

The caliper thickness, which is independent of the index of refraction and/or density or material composition of the internal layers of the material under test, is then:

$$L = D - c^*([t_1-t_0]+[t_{j+1}-t_j])/2$$

This is equivalent to stating that the thickness of the material under test is equal to the spacing of the ERS minus the sum of the thickness of the air above and below the material under test inside the ERS.

The average index of refraction (of all N layers) of the material under test is then the ratio $$N\ \text{average} = (t_1 - t_j)/(T_{ERS} - ([t_1-t_0]+[t_{j+1}-t_j])).$$

Another method to implement the ERS measurement is to subtract the known or measured "empty" (i.e., no sample in THz beam) ERS interface timing from the time from the same two reflections with a sample in the THz beam. In this manner, the equivalent time delay of a double pass transmission measurement is obtained with a reflection measurement. This method offers advantages in the "empty" ERS time measurement is more stable than that for a standard transmission measurement. Both measurements require a measurement with no sample present, but the ERS reflection measurement is more stable than the purely transmission measurement and can be remeasured or corrected or calibrated with the embodiments disclosed herein.

Figure 5:
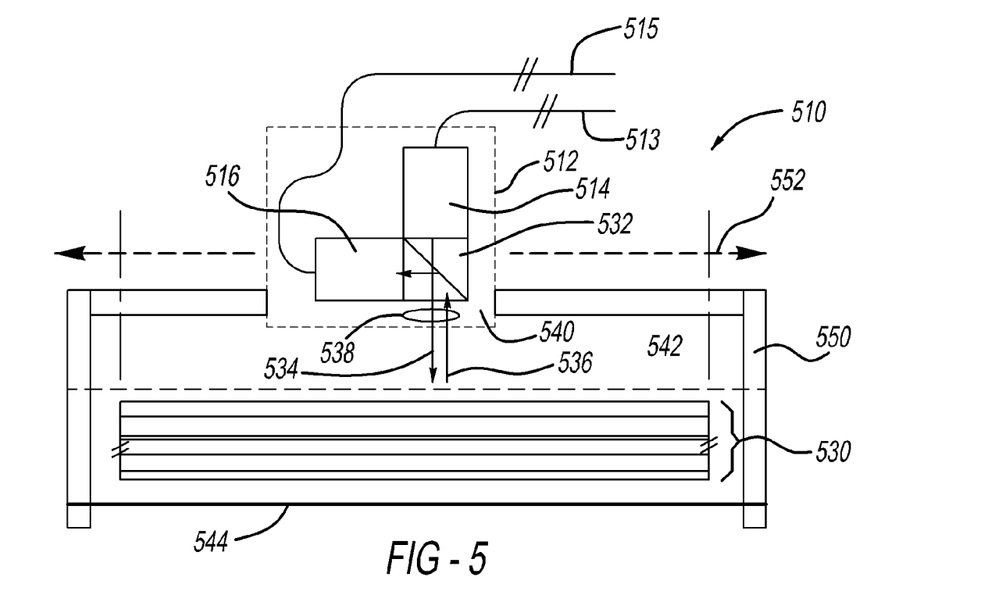
FIG. 5 illustrates a system having an optical interface that spans the width of the gantry, both above and below the material under test.

Referring to FIG. 5, another embodiment of the system 510 is shown. Like before similar reference numerals are used to refer to similar components. In this embodiment, the first optical interface 542 is located above the sample 530, while the second optical interface 544 is located below the sample 530.

Figure 6:
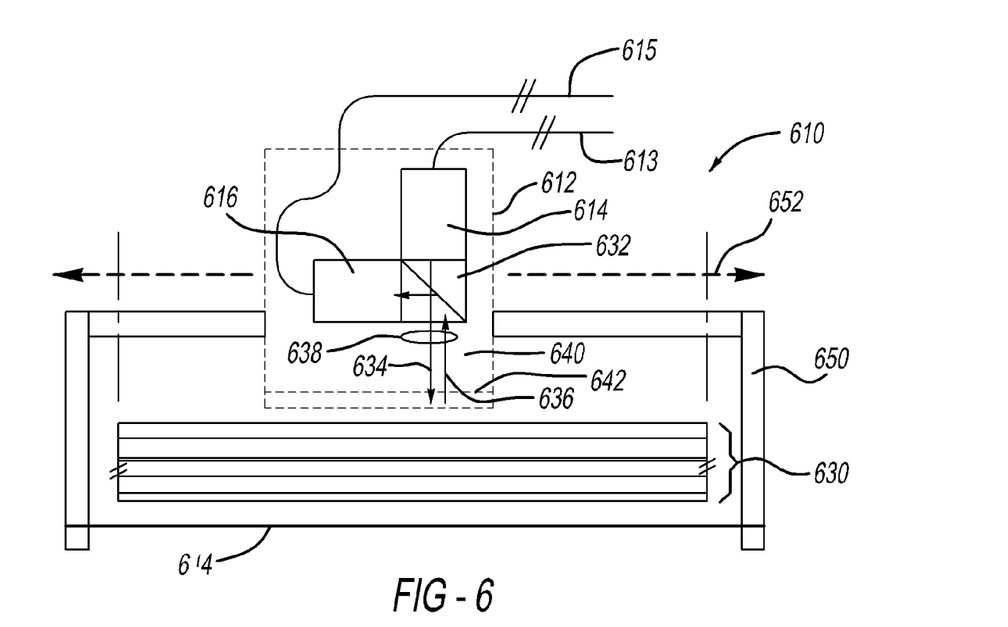
FIG. 6 illustrates the system with the first optical interface incorporated into the housing and the second optical interface spanning the width of the gantry below the material under test.
Figure 7:
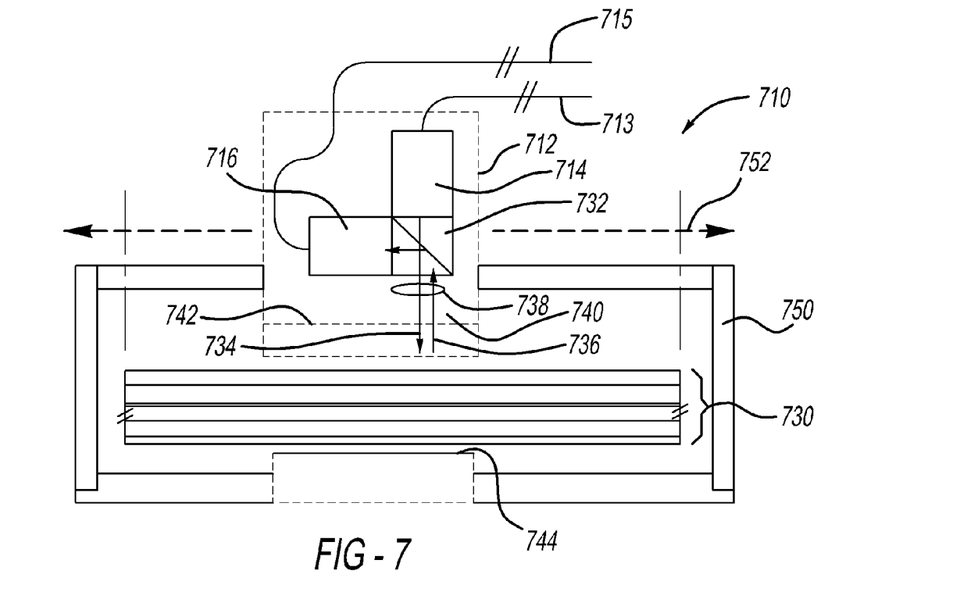
FIG. 7 illustrates the first optical interface incorporated into the housing of the system and a second optical interface mounted on a synchronized motion gantry below the material under test.

Referring to FIG. 6, another embodiment of the system 610 is shown. This embodiment differs from the embodiment of FIG. 5 in that the first optical interface 642 is located within the housing 612. Referring to FIG. 7, the embodiment of the system 710 is similar to that disclosed in FIG. 6. However, the second optical interface 744 is located on the gantry 750 such that the second optical interface 744 is directly opposite of the first optical interface 742 as the housing 712 moves along the gantry. Essentially, the second optical interface 744 has a movement that is synchronized to the movement of the housing 712 so that the second optical interface 744 can reflect terahertz radiation back to the terahertz receiver 716.

Figure 8:
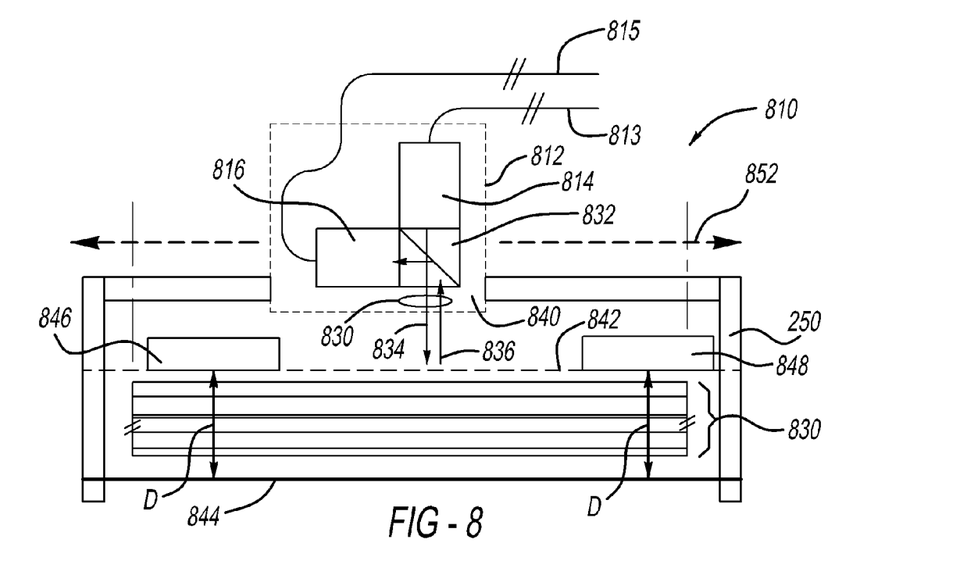
FIG. 8 illustrates a system with optical interfaces spanning the width of the gantry both above and below the material under test and distance sensors mounted on the first optical interface or gantry frame to measure the distance between the first optical interface and the second optical interface.

Referring to FIG. 8, another embodiment of the system 810 is shown. The embodiment is similar to the embodiment 510 in FIG. 5. However, the system 810 differs in that the system 810 utilizes position sensors 846 and 848 that are mounted on the first optical interface 842. The position sensors 846 and 848 may be eddy current sensors.

One aspect this embodiment is the incorporation of position sensors 846 and 848 to measure or calibrate the distance between the interfaces 842 and 844 in order to accommodate for any longer term change in geometry. Many materials under measurement are often being manufactured continuously and thus will always be present in some locations between these external reflection interfaces. Thus, any additional separation sensor(s) used to directly measure the absolute distance between the interfaces 842 and 844, must be able to do so with the material under measurement being present. That is, ideally the secondary sensor's displacement measurement cannot be affected by the presence of the sample. In general, sensors which measure the electric field, (TD-THz, optical, capacitive, microwave, etc.) are affected by the presence of a dielectric material. Magnetic sensors, such as eddy current sensors, are not substantially affected by change in the material under measurement dielectric thickness or composition or the presence of a dielectric material in the measurement path. Eddy current sensors have the required displacement measurement tolerance. Any separation or displacement sensor(s) with similar insensitivity to the material under measurement may be used as well.

Another method is to use either the THz pulses or additional separation or displacement sensors to measure the distance between the interface surfaces that by design do not interact with the sample space between the external reflection interfaces. An example of this method would be the use of a dual port THz sensor to measure the separation of the structures interfaces relative to the sensor position or another type of sensor(s) (e.g., laser, ultrasound, capacitance sensor) that measures distance to the reference structure interfaces in a method that does not interact with the sample. This measurement can be to the surface near the material under measurement or some other surface of the interface structure. The external interface may or may not be between the sensor and the material under measurement.

In another aspect, the terahertz receiver 816 can be used to measure the separation of the optical interfaces 842 and 844. THz measurements of the optical interfaces 842 and 844 can be made at locations where no sample is not present (i.e., to the "left" and "right" of the sample, referred to as "off sheet"). The THz beams can also be directed to measure the distance to one or more of the optical interfaces 842 and 844 through paths that do not interact with the sample 830 under measurement.

Figure 9:
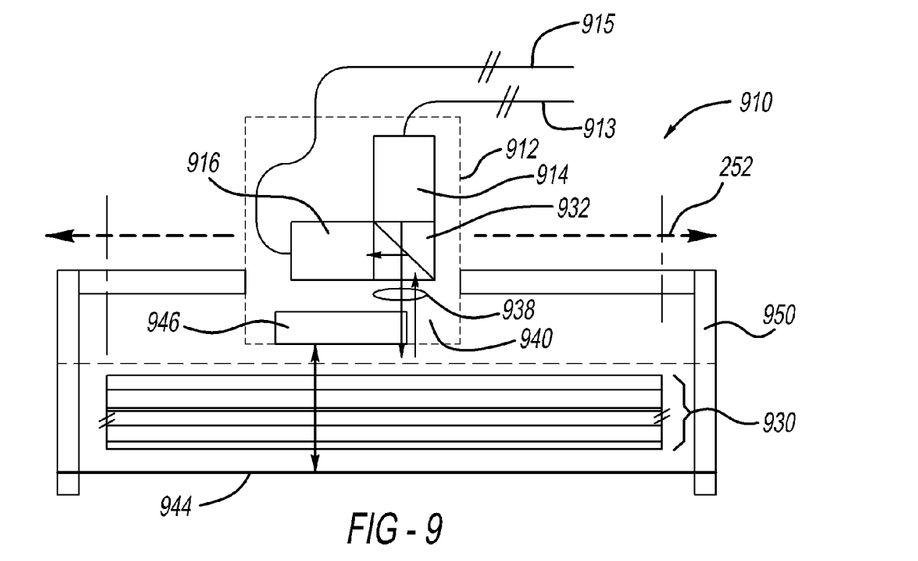
FIG. 9 illustrates a system having optical interfaces spanning the width of the gantry both above and below the material under test using a position sensor mounted in the housing.

Referring to FIG. 9, the system 910 of FIG. 9 is similar to that of the system 810 of FIG. 8; however, the position sensor 946 is located within the housing 912 of the system 910 and only one position sensor is used. Like before, the sensor 946 may be an eddy current sensor so as to determine the distance between the first optical interface 942 and the second optical interface 948.

Figure 10:
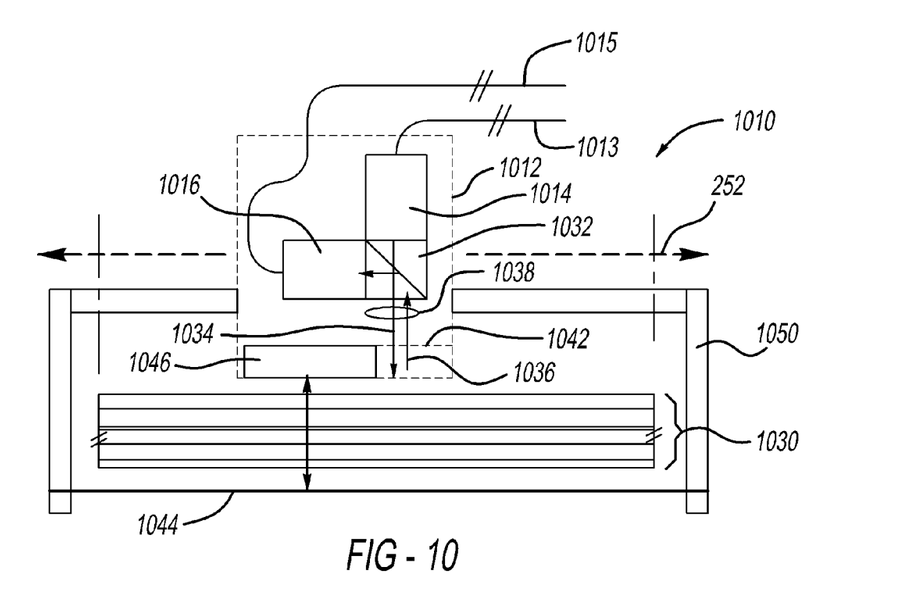
FIG. 10 illustrates a system with the first optical interface and distance sensor incorporated into the housing of the system and the second optical interface spanning the width of the gantry below the material under test.

Referring to FIG. 10, another embodiment of the system 1010 is shown. In this embodiment the housing 1012 contains both the position sensor 1048 and the first optical interface 1042.

Figure 11:
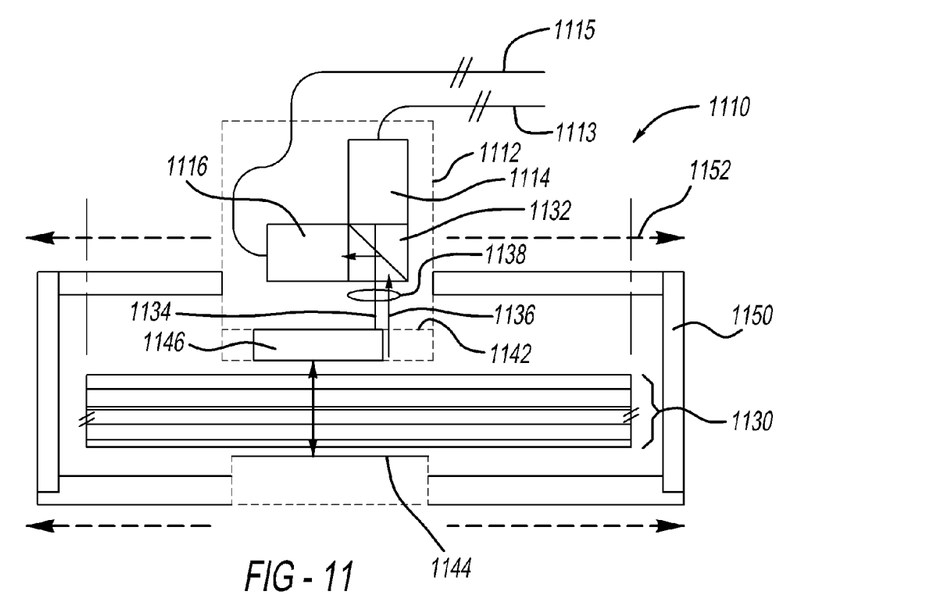
FIG. 11 illustrates a system having the first optical interface and position sensor incorporated in the housing and a second optical interface mounted on a synchronized motion gantry below the material under test.
Figure 12:
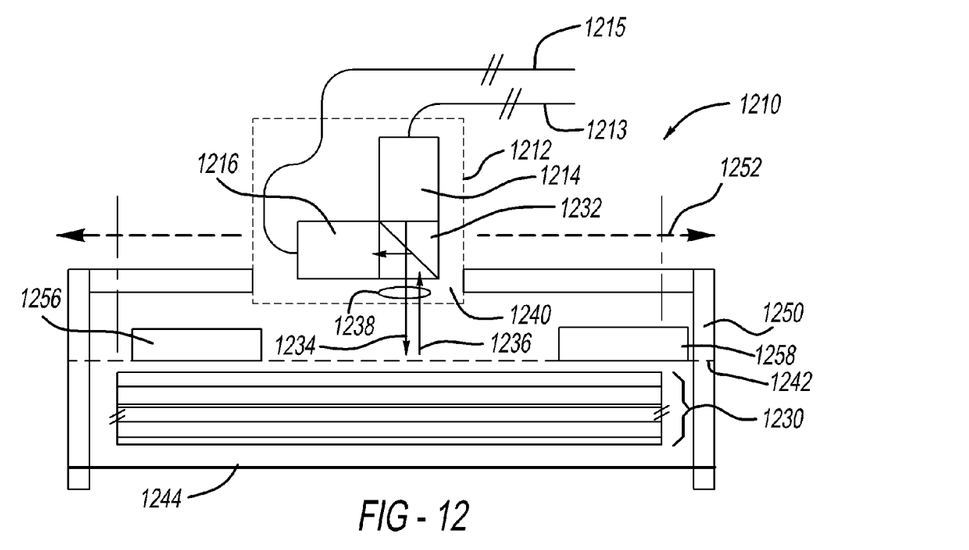
FIG. 12 illustrates a system utilizing temperature sensors mounted on the first optical interface or gantry.

Referring to FIG. 11, this embodiment is similar to the embodiment shown in FIG. 10, however, in this embodiment the second optical interface is mounted on the gantry 1150 such that the second optical interface 1146 is directly opposite of the first optical interface 1144 when the gantry moves the housing 1112. Referring to FIG. 12, the embodiment 1210 discloses a similar embodiment shown in FIG. 8; however, in this embodiment temperature sensors 1256 and 1258 are utilized.

Temperature

Figure 13:
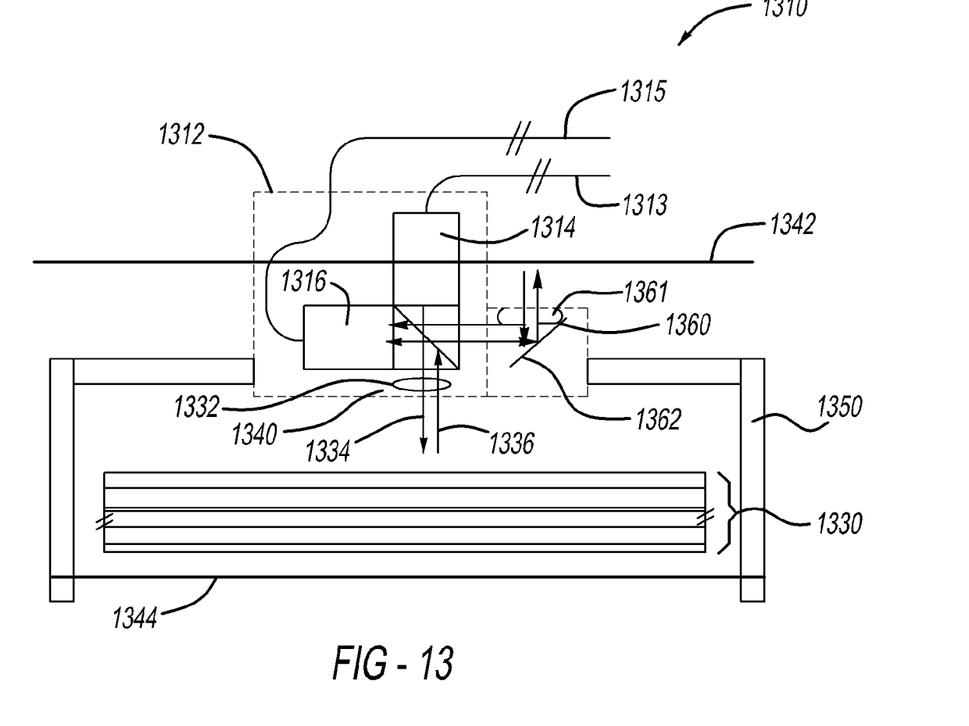
FIG. 13 illustrates a system having a first port and a second port.

Referring to FIG. 13, the system 1310 includes a second port 1360 with a beam directing device 1362, which directs terahertz radiation from the terahertz transmitter via the beam splitting device 1332, through a second port 1360 to the first optical interface 1342. This embodiment allows the first optical interface 1342 to be placed at various positions. This embodiment allows for the first optical interface 1342 to be completely reflective, such as a mirror. A lens 1361 may be placed by the port 1360 to focus the radiation to the first optical interface 1342.

As a person skilled in the art will readily appreciate, the above description is meant as an illustration of implementation of the principles this invention. This description is not intended to limit the scope or application of this invention in that the invention is susceptible to modification, variation and change, without departing from the spirit of this invention, as defined in the following claims.

We claim:

1. A system for interpreting terahertz radiation, the system comprising:
    a terahertz transmitter configured to output a pulse of terahertz radiation through a first port;
    a terahertz receiver configured to receive at least a portion of the pulse of terahertz radiation through the first port, wherein the terahertz receiver is configured to output a signal based on the radiation received by the terahertz receiver;
    a first optical interface providing optical interference to the pulse of terahertz radiation, wherein the first optical interface will reflect a first optical interface reflected portion of the pulse of terahertz radiation to the terahertz receiver;
    a second optical interface providing optical interference to the pulse of terahertz radiation, wherein the second optical interface will reflect a second optical interface reflected portion of the pulse of terahertz radiation to the terahertz receiver;
    a spacing being defined between the first optical interface and the second optical interface, wherein the first and second optical interfaces generally face one another to define the spacing, the spacing being configured to receive a sample to be irradiated by at least a portion of the pulse of terahertz radiation;
    wherein the sample will reflect a first sample reflected portion of the pulse of terahertz radiation to the terahertz receiver and a second sample reflected portion of the pulse of terahertz radiation to the terahertz receiver;
    wherein terahertz transmitter and terahertz receiver are disposed substantially adjacent to one another in a housing; and
    a processor in communication with the terahertz receiver and configured to receive the signal from the terahertz receiver, the processor being configured to determine caliper thickness, density, index of refraction or mass of the sample based on the signal.

2. The system of claim 1, further comprising a gantry, the housing being coupled to the gantry, wherein the gantry is configured to move the housing across the sample.

3. The system of claim 2, where the first optical interface is mounted to the housing.

4. The system of claim 3, where the second optical interface is mounted to the gantry, wherein the second optical interface moves as the housing moves along the gantry, wherein the first and second optical interfaces generally oppose each other.

5. The system of claim 1, further comprising a position sensor in communication with the processor, the position sensor being configured to determine the distance of the spacing between the first optical interface and the second optical interface and output a distance signal to the processor.

6. The system of claim 5, wherein the position sensor is an eddy current sensor.

7. The system of claim 6, wherein the eddy current sensor is mounted to the first optical interface.

8. The system of claim 6, wherein the eddy current sensor is mounted to the housing.

9. The system of claim 5, wherein the position sensor is a temperature sensor, the temperature sensor being configured to measure the temperature of the sample.

10. The system of claim 1, wherein the first optical interface is located between the terahertz transmitter and the sample.

11. The system of claim 10, wherein the first optical interface is coupled to the housing.

12. The system of claim 1, wherein the first port further comprises a lens.

13. The system of claim 1, wherein the sample comprises at least one layer.

14. The system of claim 1, wherein the first optical interface is a transmissive reflection surface and the second optical interface is a fully reflective optical interface.

15. The system of claim 1, further comprising:
    a second port, wherein the terahertz transmitter configured to output a pulse of terahertz radiation through the second port;
    the terahertz receiver configured to receive at least a portion of the pulse of terahertz radiation through the second port; and
    wherein the first optical interface is a fully reflective optical interface.

16. The system of claim 1, further comprising:
    an optical source configured to output optical pulses;
    wherein the optical source is in optical communication with the terahertz transmitter and the terahertz receiver; and
    wherein with the terahertz transmitter and the terahertz receiver are synchronized to receive optical pulses from the optical source such that the terahertz receiver is synchronized to the terahertz transmitter by the optical pulses.

17. The system of claim 16, further comprising a beam splitter configured to direct radiation reflected by the first optical interface, second optical interface or sample to the terahertz receiver.

18. The system of claim 16, wherein the optical source is in optical communication with the terahertz transmitter or the terahertz receiver via an optical fiber.

19. The system of claim 1, wherein:
    the first optical interface reflected portion being a portion of the terahertz radiation reflected by the first optical interface before the sample is irradiated by at least a portion of the pulse of terahertz radiation; and
    the second optical interface reflected portion being a portion of the terahertz radiation reflected by the second optical interface after the sample is irradiated by at least a portion of the pulse of terahertz radiation.

20. The system of claim 1, wherein first and second optical interfaces each have a surface that generally defines a plane, wherein the plane of each surface of the first and second optical interfaces are substantially parallel to one another.

* * * * *